(12) United States Patent
Walker

(10) Patent No.: US 6,340,384 B1
(45) Date of Patent: Jan. 22, 2002

(54) COPPER/AMINE OXIDE WOOD PRESERVATIVES

(75) Inventor: Leigh Walker, Macungie, PA (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 09/577,331

(22) Filed: May 24, 2000

Related U.S. Application Data

(60) Provisional application No. 60/135,539, filed on May 24, 1999.

(51) Int. Cl.$^7$ .......................... A01N 33/02; A01N 59/20
(52) U.S. Cl. ................... 106/18.32; 424/630; 424/635; 424/638; 424/719; 514/642; 514/644; 514/500
(58) Field of Search ................... 106/18.32; 424/630, 424/635, 638, 719; 514/642, 644, 500

(56) References Cited

U.S. PATENT DOCUMENTS

| | | | |
|---|---|---|---|
| 3,296,145 A | 1/1967 | Findlan et al. ............... 252/106 |
| 3,484,523 A | 12/1969 | Findlan et al. ............... 424/248 |
| 3,761,488 A | 9/1973 | Lewis et al. ................. 260/302 |
| 4,005,193 A | 1/1977 | Green et al. ................. 424/168 |
| 4,048,324 A | * 9/1977 | Kohn .......................... 514/500 |
| 4,076,516 A | * 2/1978 | Vartiak et al. ............... 504/152 |
| 4,089,945 A | * 5/1978 | Brinkman et al. .......... 424/702 |
| 4,105,431 A | 8/1978 | Lewis et al. .................... 71/67 |
| 4,379,810 A | 4/1983 | Amundsen et al. ......... 428/541 |
| 4,382,105 A | 5/1983 | Amundson et al. ......... 427/370 |
| 4,622,248 A | 11/1986 | Leach et al. ................. 427/440 |
| 4,761,179 A | * 8/1988 | Goettsche et al. ....... 106/18.32 |
| 4,857,322 A | 8/1989 | Goettsche et al. .......... 424/633 |
| 4,929,454 A | 5/1990 | Findlay et al. ............... 424/638 |
| 4,937,143 A | 6/1990 | West ......................... 427/419.8 |
| 4,950,685 A | 8/1990 | Ward .......................... 514/479 |
| 5,021,187 A | * 6/1991 | Harriott et al. ......... 252/186.38 |
| 5,073,570 A | 12/1991 | Tseng .......................... 514/533 |
| 5,276,029 A | 1/1994 | Goettsche et al. ....... 514/231.2 |
| 5,304,237 A | 4/1994 | Barth et al. ................. 106/18.3 |
| 5,426,121 A | 6/1995 | Bell ............................. 514/500 |
| 5,468,284 A | 11/1995 | Sturm ............................. 106/2 |
| 5,527,384 A | 6/1996 | Williams et al. ......... 106/18.32 |
| 5,536,505 A | 7/1996 | Yu .......................... 106/18.33 |
| 5,833,741 A | 11/1998 | Walker ........................... 106/2 |
| 5,972,971 A | * 10/1999 | Heuer et al. ................. 514/341 |
| 6,180,672 B1 | 1/2001 | Lichtenberg et al. ....... 514/561 |

FOREIGN PATENT DOCUMENTS

| | | | |
|---|---|---|---|
| CA | 1 174 005 | 9/1984 | .......... A01N/31/14 |
| DE | 3743 821 A1 | 7/1989 | ............ B27K/3/34 |
| DE | 4217 882 A1 | 12/1993 | .......... A01N/55/04 |
| DE | 44 41 674 A1 | 5/1996 | ......... C07C/275/32 |
| DE | 196 40 874 | 4/1998 | ............ B27K/3/34 |
| DE | 196 48 888 A1 | 5/1998 | ............ B27K/3/50 |
| EP | 0 370 182 | 5/1990 | ............ B27K/3/50 |
| EP | 0 381 482 | 8/1990 | ............ B27K/3/50 |
| EP | 0 571 846 A1 | 12/1993 | .......... A01N/47/12 |
| EP | 97/01423 | 1/1997 | ............ B27K/3/50 |
| JP | 57022003 | 2/1982 | ............ B27K/3/52 |
| JP | 64-1796 | 1/1989 | ............ C11D/3/28 |
| JP | 1-268605 | 10/1989 | .......... A01N/33/24 |
| WO | 98/00008 | 1/1998 | .......... A01N/25/02 |
| WO | 98/18321 | 5/1998 | .......... A01N/25/30 |
| WO | 98/31518 | 7/1998 | ............ B27K/3/00 |

OTHER PUBLICATIONS

American Wood Preservers' Associated, P5–Waterborne Preservatives, 4–5, 1998, (no month).
Encyclopedia of Chemical Technology, vol. 2, pp. 259–271, John Wiley & Sons Inc., 1978, (no month).
Archer et al., Forest Products Journal, 45(1):86–89, Jan. 1995.
Hirobumi et al., 120:301698 abstract of JP 05–311196 (Nov. 1993).
Liu et al., 25$^{th}$ Annual Meeting of the International Research Group on Wood Preservation, Nusa Dua Bali, Indonesia, May 29, 1994–Jun. 3. 1994.
Nicholas et al., 28$^{th}$ Annual Meeting of the International Research Group on Wood Preservation, Whistler, Canada, May 25, 1997–May 30, 1997.
Williams et al., American Wood–Perservers' Association, 90:156–176, 1994, (no month).

* cited by examiner

*Primary Examiner*—Anthony Green
(74) *Attorney, Agent, or Firm*—Darby & Darby

(57) ABSTRACT

The present invention provides a composition comprising an amine oxide and an aqueous copper amine complex. Another embodiment of the present invention is a method for preserving and/or waterproofing a wood substrate by contacting the composition with the wood substrate. Yet another embodiment is an article comprising a wood substrate and the composition of the present invention. This composition has high efficacy against fungi, including copper tolerant fungi such as brown rot and soft rot, and is phase stable at high concentrations. Additionally, the amine oxide in the composition may impart waterproofing properties. The composition of the present invention is halide free and is environmentally friendly.

26 Claims, No Drawings

COPPER/AMINE OXIDE WOOD PRESERVATIVES

This application claims the benefit of U.S. Ser. No. 60/135,539, filed May 24, 1999.

FIELD OF THE INVENTION

This invention relates to wood preservative and waterproofing compositions containing an amine oxide and an aqueous copper amine complex.

BACKGROUND OF THE INVENTION

Chromated copper arsenate is commonly employed as a wood preservative. The chromium oxidizes the wood and generates sites for fixing the copper and arsenic to the wood. Although copper is a highly effective wood preservative, some fungi are resistant to its biocidal activity. The arsenic serves to control fungi that are tolerant to copper and protect the wood against wood destroying insects.

In recent years, however, many concerns have been raised regarding contamination of the environment by chromium and arsenic. There is also increasing concern regarding disposal of wood treated with chromated copper arsenate and halides.

As a result, there is a need for copper containing wood preservatives which do not contain chromium, arsenic, or halides and are environmentally friendly, yet have similar wood preservative properties to chromated copper arsenate.

SUMMARY OF THE INVENTION

Applicants have discovered that amine oxides enhance the performance of aqueous copper amine complexes as wood preservatives and provide waterproofing properties. The present invention provides a composition comprising an amine oxide and an aqueous copper amine complex.

Another embodiment of the present invention is a method for preserving and/or waterproofing a wood substrate by contacting the composition with the wood substrate.

Yet another embodiment is an article comprising a wood substrate and the composition of the present invention.

This composition has high efficacy against fungi, including copper tolerant fungi such as brown rot and soft rot. Also, the composition is phase stable at high concentrations without the need for polyamines or other stabilizers known in the prior art. The amine oxide in the composition may impart waterproofing properties. The composition of the present invention is typically free of ionic halides, in particular chlorides, and is environmentally friendly.

DETAILED DESCRIPTION OF THE INVENTION

The present invention provides a composition comprising an amine oxide and an aqueous copper amine complex.

The amine oxide may be a trialkylamine oxide; N-alkylated cyclic amine oxide; a dialkylpiperazine di-N-oxide; an alkyldi(poly(oxyalkylene))amine oxide; a dialkylbenzylamine oxide; a fatty acylaminopropyldimethylamine oxide; a diamine dioxide; a triamine trioxide; and any combination of any of the foregoing.

Preferred trialkylamine oxides have the formula $R^1R^2R^3N\rightarrow O$, where $R^1$ is a linear, branched, cyclic or any combination thereof $C_6$ to $C_{40}$ saturated or unsaturated group; and $R^2$ and $R^3$ independently are linear, branched, or any combination thereof $C_1$ to $C_{40}$ saturated or unsaturated groups. $R^1$, $R^2$, and $R^3$ independently may be alkyl, alkenyl, or alkynyl groups. $R^1$ is preferably a $C_8$ to $C_{40}$ group. More preferably, $R^1$ is a linear, branched, cyclic or any combination thereof $C_8$ to $C_{22}$ saturated or unsaturated group, such as coco, hydrogenated tallow, soya, decyl, and hexadecyl; and $R^2$ and $R^3$ independently are linear, branched, or any combination thereof $C_1$ to $C_{22}$ saturated or unsaturated groups, such as coco, hydrogenated tallow (which is typically about 70–75% by weight of $C_1$. alkyl, about 20–25% by weight of $C_{16}$ alkyl, and traces of lower derivatives), soya, decyl, and hexadecyl.

A preferred trialkylamine oxide is a dialkylmethylamine oxide having the formula $R^1R^2CH_3N\rightarrow O$, where $R^1$ and $R^2$ are defined as above. Another preferred trialkylamine oxide is an alkyldimethylamine oxide having the formula $R^1(CH_3)_2N\rightarrow O$, where $R^1$ is defined as above. Suitable alkyldimethylamine oxides include, but are not limited to, a $C_{10}$ alkyldimethylamine oxide, a $C_{12}$–$C_{14}$ alkyldimethylamine oxide, a $C_{16}$–$C_{18}$ alkyldimethylamine oxide, and any combination of any of the foregoing.

Preferred N-alkylated cyclic amine oxides have the formula $R^4R^5R^6N\rightarrow O$ where $R^4$ is defined as $R^1$ above and $R^5$ and $R^6$ are linked to form a cyclic group. The cyclic group typically contains from about 4 to about 10 carbon atoms and may optionally contain oxygen, sulfur, nitrogen, or any combination of any of the foregoing. More preferred N-alkylated cyclic amine oxides include, but are not limited to, an alkylmorpholine N-oxide, a dialkylpiperazine di-N-oxide, and any combination of any of the foregoing.

Preferred alkylmorpholine N-oxides have the formula

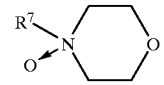

where
$R^7$ is defined as $R^1$ above.

Preferred dialkylpiperazine di-N-oxides have the formula

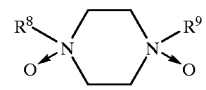

where
$R^8$ is defined as $R^1$ above and $R^9$ is defined as $R^2$ above.

Preferred alkyldi(poly(oxyalkylene))amine oxides have the formula

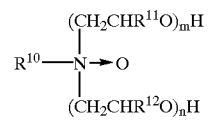

where
$R^{10}$ is defined as $R^1$ above; $R^{11}$ and $R^{12}$ independently are H or $CH_3$; and m and n independently are integers from about 1 to about 10.

Preferred dialkylbenzylamine oxides have the formula $R^{10}R^{11}R^{12}N\rightarrow O$, where $R^{10}$ is defined as $R^1$ above; $R^{11}$ is defined as $R^2$ above; and $R^{12}$ is benzyl. More preferred dialkylbenzylamine oxides include, but are not limited to, alkylbenzylmethylamine oxides having the formula $R^{10}R^{12}CH_3N\rightarrow O$ where $R^{10}$ and $R^{12}$ are defined as above.

Preferred fatty acylaminodimethylpropylamine oxides have the formula

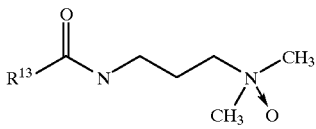

where
R$^{13}$ is defined as R$^1$ above.
Preferred diamine dioxides have the formula

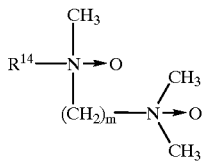

where
R$^{14}$ is defined as R$^1$ above; and m is an integer from about 1 to about 10.
Preferred triamine trioxides have the formula

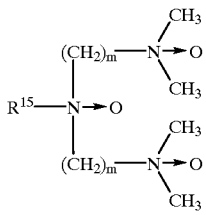

where
R$^{15}$ is defined as R$^1$ above; and m and n independently are integers from about 1 to about 10.

Long chain (C$_{16}$ or greater) amine oxides, such as hexadecylamine oxides, octadecyldimethylamine oxides, and hydrogenated tallow amine oxides, are particularly preferable for imparting waterproofing properties to the composition. Short chain (C$_{14}$ and shorter) amine oxides, such as decyldimethylamine oxides, dodecyldimethylaine oxides, and tetradecyldimethylamine oxides, aide in solubilizing the aqueous copper amine complex and long chain amine oxides, and are efficient stabilizers.

Preferably, the composition contains a mixture of C$_{16}$–C$_{18}$, long chain amine oxides to impart waterproofing properties and C$_{10}$–C$_{14}$ short chain amino oxides to solubilize the long chain amine oxides. Typically, such a mixture comprises at least 50% by weight of long chain amine oxide based upon 100% total weight of amine oxides.

A blend of long chain and short chain amine oxides is also contemplated in one embodiment of the present invention. The long chain amine oxides may be blended with the short chain amine oxides in a ratio of about from about 1:10 to 10:1 in order to yield a stable preservative solution as described herein. For example, in a preferred embodiment, a mixture of long chain (e.g., C$_{16}$) and short chain (e.g., C$_{12}$) amine oxides in a ratio of from about 1:1 to about 5:1 and particularly a ratio of about 5:2 provides the desired dissolution of copper amine complex to provide a stable solution. The appropriate ratio of long to short chain amine oxides can be readily determined by those of skill in the art using methods provided herein to test solubility and stability of the solutions.

The copper amine complex generally contains a water soluble amine. Suitable copper amine complexes include, but are not limited to, ammonium/copper complexes, ethanolamine/copper complexes, diethanolamine/copper complexes, triethanolamine/copper complexes, diethylamine/copper complexes, ethylene diamine/copper complexes, or any combination of any of the foregoing.

The weight ratio of copper (expressed as copper oxide) to amine oxide in the composition generally ranges from about 1:0.01 to about 1:50 and preferably ranges from about 1:0.5 to about 1:2. According to one embodiment, the weight ratio ranges from about 1:0.1 to about 1:5. In embodiments of the composition which include at least two amine oxides, the weight ratio of copper (expressed as copper oxide) to total amine oxide preferably ranges from about 1:1 to about 1:2.

The composition may further comprise a fatty amine having at least one C$_8$–C$_{40}$ alkyl group to further enhance the wood preserving and waterproofing performance of the composition. Suitable fatty amines include, but are not limited to, dialkylmethylamines; alkyldimethylamines and in particular (C$_8$ to C$_{18}$) alkyldimethylamines; dialkylamines (i.e. secondary amines); alkyl propylene diamines; and any combination of any of the foregoing. A non-limiting example of a suitable dialkylmethylamine is N,N-dioctyl-N-methylamine. Examples of suitable alkyldimethylamines include, but are not limited to, N-lauryl-N,N-dimethylamine, N-dodecyl-N,N-dimethylamine, N-hexadecyl-N,N-dimethylamine, Noctadecyl-N,N-dimethylamine, cocodimethylamine, hydrogenated tallow dimethyl amine, and any combination of any of the foregoing. A non-limiting example of a dialkylamine is N,N-dioctylamine. Examples of suitable alkyl propylene diamines include, but are not limited to, N-dodecyl propylene diamine, N-coco propylene diamine, and any combination of any of the foregoing. While most prior art copper compositions which contain fatty amines have low phase stability and require polyamines and other adjuvants to increase phase stability, compositions of the present invention which include fatty amines have high phase stability and do not require polyamines or other adjuvants.

The weight ratio of amine oxide to fatty amine in the composition broadly ranges from about 4:1 to about 1:4. A preferred embodiment of the invention has a weight ratio of cocodimethylamine oxide to cocodimethylamine or N-dodecyl propane diamine of about 1:1. For such an embodiment, the preferred weight ratio of copper (expressed as copper oxide) to amine oxide to fatty amine is about 2:1:1.

The composition is typically substantially free of ionic halides and preferably contain less than about 10 ppm (w/w) of ionic halides. In contrast, ammonia copper quats in wood treating solutions generally contain about 500 ppm chloride.

The composition may include a solvent (in addition to water), such as water miscible solvents including, but not limited to, alcohols, such as ethanol and glycols (e.g. ethylene glycol); esters; ethers, such as ethyl ether; polyethers; amine; and any combination of the foregoing.

The composition, when in concentrated form, preferably contains from about 5 to 30% by weight, and preferably from about 10 to 20% by weight, of combined amine oxide and copper amine complex (excluding water), based upon 100% weight of total composition.

The concentrate may be diluted to a range of about 0.1 to about 5% for treating wood. Use dilutions of the composition typically comprise a biocidally effective amount of the copper amine complex and a preservative enhancing and/or waterproofing effective amount of the amine oxide. Use dilutions preferably comprise from about 0.5 to about 5.0% by weight of amine oxide and from about 0.05 to about 1.0% by weight of copper (expressed as copper oxide), based upon 100% weight of total composition.

Other adjuvants may be included in the composition as known to one of ordinary skill in the art. Other biocides, fungicides and insecticides may be include in the composition. Any organic insecticide or fungicide that can be solubilized by an aqueous amine oxide solution is suitable for use in the present composition. Suitable insecticides include, but are not limited to, chloropyrifos, folpet, captafol, captan, pyrethroids, and any combination of any of the foregoing. Suitable fungicides include, but are not limited to, iodopropargyl butylcarbamate, tributyltin oxide, 2-(thiocyanomethylthio)benzothiazole, iodosulfones, azoles, isothiazalones, and any combination of any of the foregoing.

According to one embodiment, the weight ratio of amine oxide to biocide, fungicide, or insecticide ranges from about 1:0.01 to about 1:0.25 and preferably is about 1:0.1. For example, the composition may contain cocodimethylamine oxide and chlorpyrifos at a weight ratio of about 1:0.1.

The composition of the present invention may be prepared by mixing the aqueous copper amine complex, amine oxide, solvents, and adjuvants. The mixture may be heated, e.g., to a temperature of from about 50 to about 60° C., and/or stirred to expedite mixing.

A preferred method of preparing the composition is to mix the concentrated copper amine complex with the amine oxide followed by stirring and optional warming until the mixture is uniform. Water miscible solvents, such as alcohols, glycols, ethers, and the like, may be used to hasten solution of the components.

The copper amine complex may be prepared by methods known in the art. For example, U.S. Pat. No. 4,622,248 describes forming copper amine complexes by dissolving copper oxide in ammonia in the presence of ammonia bicarbonate. U.S. Pat. No. 4,622,248 also discloses an alternative method of preparing copper amine complexes by dissolving a mixture of copper carbonate and copper hydroxide in ethanolamine and water. The complexing amine and copper need to be charged to meet the 4 to 1 (molar) stoichiometry and thus the weight ratio of reagents will be different for each complexing amine. For amino with more than one amine group such as ethylene diamine, each amine group may be counted in the calculation.

Another embodiment of the present invention is a method for preserving and/or waterproofing a wood substrate by contacting a wood substrate with the composition of the present invention. The composition may be applied by any wood treating method known to one of ordinary skill in the art including, but not limited to, brushing, dipping, soaking, vacuum impregnation (e.g. double vacuum technique), and pressure treatment using various cycles.

EXAMPLES

The following examples illustrate the invention without limitation. All parts and percentages are given by weight unless otherwise indicated. All of the amine oxides in the examples are dimethylamine oxides unless otherwise indicated.

Example 1

(I) An aqueous solution of ammoniated copper carbonate was prepared by mixing 10 g of copper oxide (CuO) in 27 g of ammonia, 17 g of ammonium carbonate, and 46 g of water and stirring to yield 100 g of 10% (by weight) CuO concentrate.

(II) An aqueous solution of copper ethanolamine complex was prepared by dissolving 14 g of copper carbonate/hydroxide ($CuCO_3 \cdot Cu(OH)_2$) (also known as basic copper carbonate), available from Aldrich Chemical Co. of Milwaukee, Wis., in 30 g of ethanolamine and 56 g water and stirring to yield 100 g of 10% CuO concentrate.

The maximum concentration of ammoniated copper carbonate or copper ethanolamine in the mixtures with various amine oxides and fatty amines was determined. The solutions were prepared by mixing one of the prepared copper mixtures (I) or (II) with the amine oxides and adjuvants listed in Table 1. Hot tap water and/or stirring was occasionally performed to hasten mixing of the components.

Prior art combinations were also tested for comparison. Amine (or Ammonia) Copper Quats (ACQs) (i.e. the first five mixtures in Table 1) were prepared as described in U.S. Pat. No. 4,929,454.

The solution was then observed to determine the number of phases in the solution. For dark solutions, a small sample of the solution was transferred to a thin tube, placed in front of a light, and observed. If more than one phase was observed, increments of water were added to the solution, the solution warmed and shaken, and observed again. This procedure was repeated until the solution was a clear single phase at room temperature. The results are shown in Table 1 below.

TABLE 1

| Amine of Copper Amine Complex | Amine Oxide or other Co-reagent | Adjuvant | Weight Ratio of Copper (expressed as copper oxide) to Amine Oxide (or Co-reagent) to Adjuvant | Maximum Copper Possible in Clear Single Phase (% w/w) (expressed as copper oxide) |
|---|---|---|---|---|
| Ammonia | DDAC | — | 2:1 | 2 |
| Ammonia | DDAC | — | 1:1 | 1 |
| Ammonia | Didecyldimethyl-ammonium carbonate | — | 2:1 | 5 |
| Ethanolamine | DDAC | — | 2:1 | 5 |
| Diethanolamine | DDAC | — | 2:1 | 5 |
| Ammonia | $C_{10}$–$C_{14}$ amine oxides, including coco amine oxide, individually or mixed | — | 2:1 | ≧9 |

TABLE 1-continued

| Amine of Copper Amine Complex | Amine Oxide or other Co-reagent | Adjuvant | Weight Ratio of Copper (expressed as copper oxide) to Amine Oxide (or Co-reagent) to Adjuvant | Maximum Copper Possible in Clear Single Phase (% w/w) (expressed as copper oxide) |
|---|---|---|---|---|
| Ammonia | $C_{12}$ amine oxide | — | 3:1, 1:1, and 1:5 | ≧9 |
| Ethanolamine | $C_{10}$–$C_{14}$ amine oxides, including coco amine oxide, individually or mixed | — | 2:1 and 1:1 | ≧9 |
| Ammonia or Ethanolamine | $C_{12}$–$C_{18}$ amine oxide at a weight ratio of 1:1 | — | 2:1 to 1:1 | ≧9 |
| Ammonia | $C_{10}$ amine oxide and $C_{16}$ amine oxide at a weight ratio of 1:1 | — | 2:1 to 1:1 | ≧9 |
| Ammonia | $C_{16}$ amine oxide | — | 2:1 | Solid at 30° C. at 5% copper |
| Ammonia | $C_{12}$ amine oxide and $C_{16}$ amine oxide | — | 1:0.5 ($C_{12}$): 1.7 ($C_{16}$) | 6 (but the solution was thick) |
| Ammonia | $C_{12}$ amine oxide | cocodimethylamine | 2:1:1 | ≧8.5 |
| Ammonia | $C_{12}$ amine oxide | dodecylpropane diamine | 1:0.5:0.5 | ≧8.5 |
| Ammonia | None (CONTROL) | cocodimethylamine | 2:1 | <1 |
| Ethanolamine | $C_{12}$ amine oxide | dodecylpropane diamine | 1:0.2:0.6 | ≧1 |
| Ethanolamine | None (CONTROL) | dodecylpropane diamine | 1:0.6 | <1 |
| Ammonia | $C_{12}$ amine oxide | $C_{18}$ amine | 1:0.5:0.25 | ≧8.5 |
| Ammonia | $C_{12}$ amine oxide | Chlorpyrifos | 1:0.5:1 | ≧8.5 |

DDAC is N,N-didecyl-N,N-dimethylammonium chloride.

Prior art test solutions containing quaternary ammonium compounds were prepared and the maximum copper concentration was determined as above. The results are shown in Table 2 below. The results shown in Table 1 demonstrate that solutions having a copper concentration equal to or greater than 10% of copper were possible with amine oxides of various types and in varying ratios, yielding clear stable concentrated solutions. In contrast, solutions containing high concentration of copper quaternary ammonium compounds (prior art systems) were not successfully obtained.

Example 2

The following experiments were performed to determine the wood treating properties of the compositions of the invention. The following solutions were prepared:

(A) Copper Ammonia/Dodecyldimethylamine Oxide Treating Solution 480 g of ammoniated copper carbonate concentrate prepared as in Example 1 (i.e. solution (I)) was mixed with 160 grams of Barlox® 12, which is a 30% (w/w) aqueous solution of dodccyldimethylamine oxide available from Lonza, Inc., of Fair Lawn, N.J., to yield a concentrated solution. This solution was diluted with 7360 grams of deionized water and the resulting solution containing 0.6% (w/w) copper oxide and 0.6% dodecyldimethylamine oxdie was used to treat wood in a pressure cylinder.

(B) Copper Ammonia/Dodccyldimethylamine Oxide/Hexadecyldimethylamine Oxide Treating Solution An aqueous amine oxide solution was prepared by mixing 267 grams of Barlox® 16S, which is a 30% (w/w) aqueous solution of hexadecyldimethylamine oxide available from Lonza, Inc.; 107 grams of Barlox® 12 (32 g of dodecyldimethylamine oxide); and 500 g of deionized water. 480 g of ammoniated copper carbonate concentrate prepared as in Example 1 (i.e. solution (I)) was mixed with the aqueous amine oxide solution to yield a concentrated solution. This solution was diluted with 6650 grams of deionized water and the resulting solution (containing 0.6% copper oxide, 1.0% hexadecyldimethylamine oxide, and 0.4% dodecyldimethylamine oxide) was used to treat wood in a pressure cylinder.

(C) Copper Ethanolamine/Dodecyldimethylamine Oxide/Hexadecyldimethylamine Oxide Treating Solution 480 g of copper ethanolamine solution prepared as in Example 1 (i.e. solution (II)) was mixed with the aqueous amine oxide (precursor) solution prepared in Example 2(B) to yield a concentrated solution. This solution was diluted with 6650 grams of deionized water and the resulting solution (containing 0.6% copper oxide, 1.0% hexadecyldimethylamine oxide, and 0.4% dodecyldimethylamine oxide) was used to treat wood in a pressure cylinder.

(D) Copper Ammonia/Dodecyldimethylamine Oxide/Fatty Amine Treating Solution 480 g of ammoniated copper carbonate concentrate prepared as in Example 1 (solution (1)) was mixed with 80 grams of Barlox® 12 (24 grams of dodecyldimethylamine oxide), and 24 grams of Barlene# $12C_{which\ is}$ 100% cocodimethylamine containing a range of alkyl groups from 8 to 18 carbon atoms and is available from Lonza, Inc., to yield a concentrated solution. This solution was diluted with 7400 grams of deionized water to yield a solution containing 0.5% copper oxide, 0.3% dodecylamine oxide, and 0.3% cocodimethylamine. This solution was used to treat wood in a pressure cylinder.

(E) Copper Ammonia/Dodecyldimethylamine Oxide Treating Solution for Insect Control in Wood 4.8 g technical (not purified) chlorpyrifos solid was dissolved in 160 grams of Barlox® 12 (48 g of dodecyldimethylamine oxide). This solution was mixed with 480 g of ammoniated copper carbonate concentrate prepared as in Example 1 (solution (1)) to yield a concentrated solution. The concentrated solution was diluted with 7360 grams of deionized water and the resulting solution containing 0.6% copper oxide, 0.6% dodecyldimethylamine oxide, and 0.06% chlorpyrifos was used to treat wood in a pressure cylinder.

method compares the rate of growth on the fungi on an agar medium that is impregnated with various levels of the test compound. A dose response is obtained which relates how the particular chemical combinations will retard fungal growth on a natural media. The concentration at which 50% retardation of the growth of the particular fungi is defined as the $IC_{50}$ and is a useful value to compare preservative systems.

The compositions in Table 3 below were tested against *P. placenta*, which is a copper tolerant brown rot fungus, and *C. globosum*, which is a soft rot fungus, according to this method. The results are shown in Table 3 below.

TABLE 3

$IC_{50}$ of Copper Based Combinations against *P. placenta* and *C. globosum*

| Amine of Copper Amine Type or ACQ | Amine Oxide and/or Adjuvant | Ratio copper (expressed as copper oxide) to adjuvant | $IC_{50}$ vs. *P. placenta* (ppm) | $IC_{50}$ vs. *C. globosum* (ppm) |
|---|---|---|---|---|
| Ammonia | — | — | 150 | 150 |
| Ethanolamine | — | — | 150 | 100 |
| Ammonia | DDAC | 1:0.5 | 7 | 20 |
| Ethanolamine | DDAC | 1:0.5 | 7 | 15 |
| Ammonia | dodecyldimethylamine oxide | 1:1 | 50 | 50 |
| Ethanolamine | dodecyldimethylamine oxide | 1:1 | 15 | 20 |
| Ammonia | hexadecyldimethylamine oxide and decyldimethylamine oxide $C_{16}$ & $C_{10}$ amine oxide | 1:0.7:0.3 | 5 | 20 |
| Ethanolamine | hexadecyldimethylamine oxide and decyldimethylamine oxide $C_{16}$ & $C_{10}$ amine oxide | 1:0.7:0.3 | 15 | 8 |
| Ammonia | dodecyldimethylamine oxide and cocodimethylamine | 1:0.5:1 | 8 | 5 |
| Ammonia | dodecyldimethylamine oxide and octadecyldimethylamine | 1:0.5:0.25 | 9 | 10 |

Pressure treatment experiments were carried out on 2 foot by 2 inch×4 inch pieces of kiln dried #1 grade Southern yellow pine end coated with an epoxy paint. The treating cycle involved 30 minutes at −90 kPa, injection of the test solution, pressure to 950 kPa for 30 minutes, pressure break and solution drain followed by final vacuum of −90 kPa for 30 minutes. Analysis indicated that all components in these treating solutions penetrated the wood effectively.

Example 3

Efficacy Against Copper Tolerant and Soft Rot Fungi

The agar plate method (Archer et al., *Forest Products Journal*, 1995, 45:1) was used to assess performance of the wood preservative compounds against fungal growth on wood. The principle of the test is to assess the retardation of a test organism on agar treated with the preservative. The The results demonstrate that the copper amine oxide compositions of the invention were particularly effective against both the copper tolerant brown rot fungus *P. placenta* and the soft rot fungus *C. globosuim*.

Copper only containing combinations controlled these fungi only at high levels. Table 3 shows that the copper only system required 150 ppm copper (expressed as copper oxide) to control either of these fungi. Furthermore, the compositions of the present invention, which are halide free, performed at least as well as prior art amine copper quats containing DDAC.

Example 4

The following experiment was performed to evaluate the waterproofing properties of the compositions of the present invention. ¼"×¾"×6" ponderosa pine end grain wafers were treated with the test solutions prepared in Example 1 using a double vacuum method. Each wood sample was evacuated in a vacuum desiccator to about −80 kPa pressure. A test solution was injected into the chamber and the vacuum was released with air. Excess solution was blotted from the wood sample and the wood was returned to the desiccator on a small rack. Vacuum was drawn again to remove liquid from the wood ("kickback" solution). Samples that were subjected to weathering were placed on a flat surface outside and exposed to natural environmental weather conditions for 90 days.

The results are shown in Table 4.

TABLE 4

| Treating Compositions | Water Uptake % in 30 Minutes Soak | |
|---|---|---|
| | Freshly Treated | 100 Days Weathering |
| Untreated Control | 85 | 90 |
| 0.5% w/w (expressed as copper oxide) Copper Ammonia Complex | 54 | 79 |
| 0.5% w/w (expressed as copper oxide) Copper Ethanolamine Complex | 68 | 77 |
| 0.5% w/w Copper Ammonia Complex (expressed as copper oxide) and 0.25% w/w DDAC | 70 | 80 |
| 0.5% w/w Copper Ammonia Complex (expressed as copper oxide) with 0.25% w/w Dodecyl Dimethylamine Oxide | 70 | 77 |
| 0.5% w/w Copper Ammonia Complex (expressed as copper oxide) with 0.7% w/w Hexadecyl Dimethylamine Oxide and 0.3% w/w Dodecyl Dimethylamine Oxide | 47 | 38 |
| 0.5% w/w Copper Ethanolamine Complex (expressed as copper oxide) with 0.7% w/w Octadecyl Dimethylamine Oxide and 0.3% w/w Dodecyl Dimethylamine Oxide | 42 | 40 |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A composition comprising:
   (a) a preservative enhancing or waterproofing effective amount of one or more amine oxides, and
   (b) a biocidally effective amount of one or more aqueous copper amine complexes,
wherein the composition is substantially free of chlorides.

2. The composition of claim 1, wherein the amine oxide is selected from the group consisting of trialkylamine oxide; N-alkylated cyclic amine oxides; a dialkylpiperazine di-N-oxide; a dialkylbenzylamine oxide; a fatty acylaminopropyldimethylamine oxide; a diamine dioxide; a triamine trioxide; and any combination of any of the foregoing.

3. The composition of claim 2, wherein the trialkylamine oxide has the formula $R^1R^2CH_3N \rightarrow O$, wherein $R^1$ is a linear, branched, cyclic, or any combination thereof $C_6$ to $C_{40}$ saturated or unsaturated group; and $R^2$ and $R^3$ are independently linear, branched, cyclic, or any combination thereof $C_1$ to $C_{40}$ saturated or unsaturated groups.

4. The composition of claim 3, wherein $R^1$ is a linear, branched, cyclic, or any combination thereof $C_8$ to $C_{22}$ saturated or unsaturated group; and $R^2$ and $R^3$ are independently linear, branched, cyclic, or any combination thereof $C_1$ to $C_{22}$ saturated or unsaturated groups.

5. The composition of claim 3, wherein the trialkylamine oxide is an alkyldimethylmine oxide having the formula $R^1(CH_3)_2N \rightarrow O$, wherein $R^1$ is a linear, branched, cyclic, or any combination thereof $C_6$ to $C_{40}$ saturated or unsaturated group.

6. The composition of claim 5, wherein $R^1$ is a a linear, branched, cyclic, or any combination thereof $C_8$ to $C_{22}$ saturated or unsaturated group.

7. The composition of claim 6, wherein $R^1$ is a $C_{12}$ to $C_{14}$ saturated or unsaturated linear, branched, cyclic, or any combination thereof alkyl group.

8. The composition of claim 6, wherein $R^1$ is a $C_{16}$ to $C_{18}$ saturated or unsaturated linear, branched, cyclic, or any combination thereof alkyl group.

9. The composition of claim 6, wherein $R^1$ is a $C_{10}$ saturated or unsaturated linear, branched, cyclic, or combination thereof alkyl group.

10. The composition of claim 1, wherein the copper amine complex comprises a water soluble amine.

11. The composition of claim 10, wherein the amine is selected from the group consisting of ammonia, ethanol amine, diethanolamine, triethanolamine, diethylamine, and ethylene amine.

12. The composition of claim 1, wherein the copper amine complex is an ammonium/copper complex, an ethanolamine/copper complex, a diethanolamine/copper complex, a triethanolamine/copper complex, a diethylamine/copper complex, an ethylene diamine/copper complex, or any combination of any of the foregoing.

13. The composition of claim 1, wherein the copper amine complex comprises from about 0.05 to about 5.0% by weight of copper (expressed as copper oxide), based upon 100% weight of total composition.

14. The composition of claim 1, wherein the copper amine complex comprises from about 0.5 to about 1.0% by weight of copper oxide, based upon 100% weight of total composition.

15. The composition of claim 1, wherein the copper and the amine oxide are present at a weight ratio range of from about 1:0.1 to about 1:5.

16. The composition of claim 15, wherein the weight ratio ranges from about 1:0.5 to about 1:2.

17. The composition of claim 1 further comprising one or more fatty amines having at least one $C_8$–$C_{40}$ alkyl group.

18. The composition of claim 17, wherein the fatty amine has at least one $C_8$–$C_{40}$ alkyl group.

19. The composition of claim 18, wherein the fatty amine is selected from the group consisting of ($C_8$ to $C_{18}$) alkyldimethylamines, cocodimethylamine, hydrogenated tallow dimethyl amine, dioctylamine, N-dodecyl propylene diamine, N-coco propylene diamine, N-coco propane diamine, and any combination of any of the foregoing.

20. The composition of claim 17, wherein the weight ratio of the amine oxide to the fatty amine ranges from about 4:1 to about 1:4.

21. The composition of claim 1, further comprising an insecticide, fungicide, or any combination thereof.

22. The composition of claim 1, further comprising a solvent.

23. The composition of claim 22, wherein the solvent is an alcohol, glycol, or ether.

24. A method for preserving a wood substrate, the method comprising contacting the wood substrate with a biocidally effective and preservative enhancing amount of the composition of claim 1.

25. A method for waterproofing a wood substrate, the method comprising contacting the wood substrate with a waterproofing effective amount of the composition of claim 1.

26. An article comprising
  (A) wood substrate; and
  (B) a biocidally effective amount of a composition as defined in claim 1.

* * * * *